United States Patent
Buettner et al.

(10) Patent No.: US 7,449,610 B2
(45) Date of Patent: Nov. 11, 2008

(54) METHOD FOR EXTRACTING NITROCRESOLS FROM WASTE WATER PRODUCED IN THE MANUFACTURE OF MONONITROTOLUENE AND USE OF SAID EXTRACT

(75) Inventors: Johannes Buettner, Ruhland (DE); Holger Allardt, Schwarzheide (DE); Reinhard Tonder, Klettwitz (DE); Reiner Reetz, Schwarzheide (DE); Michael Reichelt, Ruhland (DE)

(73) Assignee: BASF SE, Ludwigshafen (DE)

( * ) Notice: Subject to any disclaimer, the term of this patent is extended or adjusted under 35 U.S.C. 154(b) by 271 days.

(21) Appl. No.: 10/573,020

(22) PCT Filed: Sep. 18, 2004

(86) PCT No.: PCT/EP2004/010497

§ 371 (c)(1), (2), (4) Date: Mar. 22, 2006

(87) PCT Pub. No.: WO2005/037766

PCT Pub. Date: Apr. 28, 2005

(65) Prior Publication Data
US 2007/0043244 A1   Feb. 22, 2007

(30) Foreign Application Priority Data
Sep. 29, 2003   (DE)   ................. 103 45 601

(51) Int. Cl.
*C07C 205/06* (2006.01)
*C02F 1/26* (2006.01)

(52) U.S. Cl. ..................... 568/934; 568/932
(58) Field of Classification Search ............... 568/934
See application file for complete search history.

(56) References Cited

U.S. PATENT DOCUMENTS

| 4,257,986 | A |   | 3/1981 | Milligan et al. |
| 4,361,712 | A | * | 11/1982 | Herman et al. ............ 568/932 |
| 4,597,875 | A |   | 7/1986 | Carr et al. |
| 4,604,214 | A |   | 8/1986 | Carr et al. |
| 4,986,917 | A |   | 1/1991 | Adams et al. |
| 5,948,944 | A | * | 9/1999 | Zhang et al. ............ 568/934 |
| 6,506,948 | B1 | * | 1/2003 | Sawicki ............ 568/934 |
| 6,583,327 | B2 |   | 6/2003 | Demuth et al. |
| 6,936,741 | B2 | * | 8/2005 | Munnig et al. ............ 568/934 |

OTHER PUBLICATIONS

International Search Report No. PCT/EP2004/010497 dated Jan. 21, 2005, 4 pages.

* cited by examiner

*Primary Examiner*—Yvonne Eyler
*Assistant Examiner*—Yate' K Cutliff
(74) *Attorney, Agent, or Firm*—Connolly Bove Lodge & Hutz LLP

(57) ABSTRACT

The invention provides a process for removing nitrocresols from wastewater of mononitrotoluene preparation, which comprises acidifying the alkaline wastewater of mononitrotoluene preparation with acids to a pH of at most 3 and treating the nitrocresols with an extractant.

The invention further provides the preparation of dinitrotoluene by use of the nitrocresol-containing extracts as a feedstock.

18 Claims, No Drawings

METHOD FOR EXTRACTING NITROCRESOLS FROM WASTE WATER PRODUCED IN THE MANUFACTURE OF MONONITROTOLUENE AND USE OF SAID EXTRACT

CROSS REFERENCE TO RELATED APPLICATION

The present application is a National Stage application of PCT/EP2004/010497, filed Sep. 18, 2004, which claims priority from German Patent Application No. DE 103 45 601.5, filed Sep. 29, 2003.

The invention relates to a process for removing nitrocresols from the wastewater of mononitrotoluene preparation by extraction and for further use of the extract in dinitrotoluene production.

U.S. Pat. No. 4,597,875 describes the treatment of wastewater of dinitrotoluene production with sulfuric acid, in which the di- and trinitrocresols present in the wastewater are separated out as a liquid and disposed of by incineration. For the treatment of the wastewater of mononitrotoluene production, this process is of low suitability, since the nitrocresols present precipitate out as a very finely divided, solid precipitate when the wastewater of mononitrotoluene production is acidified under analogous conditions, the precipitate being very difficult to remove from the aqueous phase. Owing to the adhering residual water, the solid precipitate removed is also difficult to handle in a continuous process.

Nitrotoluene is prepared on the industrial scale by the action of a nitric acid-sulfuric acid mixture on toluene. This forms not only the mononitrotoluene isomers by oxidative action on the toluene but also various nitrocresol compounds as undesired by-products in proportions of less than one percent. Their removal from the reaction product is absolutely necessary before their further use, for example the isomer separation by distillation or melt crystallization.

To remove the nitrocresols from the crude product, the latter is typically washed first with water to remove acid traces and then with a basic solution, for example dilute sodium hydroxide solution, sodium carbonate solution or ammonia solution. This converts the relatively acidic nitrocresols virtually fully to their aqueous phase as sodium nitrocresolates. After the phase separation, the so-called mononitrotoluene wastewater, referred to below as MNT wastewater, is obtained.

In order to prepare the MNT wastewater stream of a continuous plant for the introduction into a water body utilized as a receiving body, the MNT wastewater is subjected to a biological wastewater treatment. The nitrocresols present in the MNT wastewater have been found to be difficult to biodegrade.

This gives rise to the object of developing a process which removes the nitrocresols virtually fully from the MNT wastewater and allows the nitrocresols removed to be eliminated in a simple and economically acceptable manner and to be sent to a further use.

The object has been achieved in accordance with the invention by acidifying the alkaline wastewater of the MNT preparation with acids to a pH of at most 3 and extracting the nitrocresols with an extractant, advantageously with toluene, o-, m-, p-nitrotoluene or mixtures thereof.

The invention accordingly provides a process for removing nitrocresols from wastewater of mononitrotoluene preparation, which comprises acidifying the alkaline wastewater of mononitrotoluene preparation with acids to a pH of at most 3 and treating the nitrocresols with an extractant.

The invention further provides the preparation of dinitrotoluene by use of the nitrocresol-containing extracts as a feedstock.

A process has been found in which the acidification of the alkaline MNT wastewater is combined with an extraction using a suitable liquid extractant, and the resulting nitrocresol-containing extract is fed to dinitrotoluene production as a sidestream.

To acidify the alkaline MNT wastewater, acids having a $pK_a$ value of at most 2, preferably below 1, are advantageously used. These are in particular mineral acids, for example sulfuric acid and nitric acid. Particular preference is given to using sulfuric acid or nitric acid or mixtures thereof.

The amount of acid is selected in accordance with the invention in such a way that the wastewater, after the acidification, has a pH of at most 3, advantageously a pH of at most 2.

The extraction is effected using a suitable liquid extractant. With regard to the further use of the nitrocresol-containing extract in dinitrotoluene production, the extractants used are preferably toluene or mononitrotoluenes liquid at process temperature of the extraction (o-, m-, p-nitrotoluene) or isomer mixtures thereof, or mixtures of toluene and mononitrotoluene isomers.

To achieve the inventive purpose, useful extractants are also other sparingly water-soluble organic substances liquid at process temperature, for example benzene, xylenes, n- and isoalkanes or halogenated hydrocarbons, for example carbon tetrachloride or methylene chloride.

The volume ratio of the wastewater to be extracted to the extractant should advantageously be from 1:1 to 50:1. Preference is given to working at a ratio of from 2:1 to 10:1. Particularly good results are achieved at a ratio of from 2:1 to 5:1.

With regard to the further use of the nitrocresol-containing extract in dinitrotoluene production, the extractants used are preferably toluene or mononitrotoluenes liquid at process temperature of the extraction (o-, m-, p-nitrotoluene) or isomer mixtures thereof, or mixtures of toluene and mononitrotoluene isomers.

The extraction temperature selected is advantageously, for instance, the temperature at which the MNT wastewater is obtained from the preceding scrubbing. The preferred temperature range is between 25 and 60° C., in particular between 30 and 55° C.

The sequence of metering of acid and extractant to the wastewater is arbitrary. After the addition of the two components, intensive mixing of the organic and aqueous phases should be undertaken in order to achieve the mass transfer of the nitrocresols to the organic phase. Suitable apparatus for this purpose is, for example, stirred tanks, countercurrent columns or static mixers. The subsequent phase separation is effected advantageously in static separators by natural gravity or in dynamic separators (centrifuges).

The nitrocresol-containing extractant comprises predominantly dinitrocresol, but also small amounts of mono and trinitrocresols.

It is a particular advantage of this process that the extracted nitrocresols can be used further by introducing the nitrocresol-containing extracts into a process for preparing dinitrotoluene. In this process, the majority of the extracted nitrocresols is surprisingly degraded. It would have been expected that the use of the extract would cause a distinct increase in the total content of nitrocresols in the DNT wastewater.

It is in principle unimportant whether the extracts are added as a substream to the process stage of mononitration of toluene or to the process stage of dinitration. Especially when toluene is used as the extractant, preference is given to adding the resulting extract to the process stage of mononitration of toluene. When nitrotoluene is used as the extractant, preference is given to the addition to the process stage of dinitration.

The amount of nitrocresols added to the process for preparing of dinitrotoluene by the addition of the extracts is preferably between 0.01 and 1% by weight, especially between 0.05 and 0.5% by weight, based on the amount of dinitrotoluene obtained. When these limits are complied with, no significant deterioration in the quality of the dinitrotoluene and no significant adverse influence on the disposal of the process wastewater of dinitrotoluene preparation is observed.

The advantage of the process found thus consists in the inexpensive removal of the nitrocresols from the wastewater of mononitrotoluene preparation and their simple elimination. It is also advantageous that the nitrocresols are removed almost quantitatively, no separate process step is required for their disposal, and no additional heat energy has to be supplied or removed.

The invention is illustrated in detail in the working examples which follow but without thus undertaking a corresponding restriction.

EXAMPLE 1

Extraction of MNT Wastewater with Toluene in a Ratio of 10:1

In a round-bottom flask with stirrer and dropping funnel, 1 l of alkaline MNT wastewater with a content of 2620 mg/l of dinitrocresols was mixed intensively with 0.1 l of toluene. In order to establish a pH of approx. 2, 7 ml of 93% sulfuric acid were added dropwise. Subsequently, the mixture was stirred for another 30 minutes. After the stirrer had been switched off, full phase separation was awaited. The MNT wastewater thus treated as an aqueous phase still had a residue content of dinitrocresols of 46 mg/l.

EXAMPLE 2

Extraction of MNT Wastewater with Mononitrotoluene in a Ratio of 10:1

The procedure was as in example 1 except that the 0.1 l of toluene was replaced by 0.1 l of an industrially prepared isomer mixture of the three mononitrotoluenes. The MNT wastewater thus treated as an aqueous phase still had a residue content of dinitrocresols of 32 mg/l.

EXAMPLE 3

Extraction of MNT Wastewater with Mononitrotoluene in a Ratio of 3:1

The procedure was as in example 1 except that the 0.1 l of toluene was replaced by 0.33 l of an industrially prepared isomer mixture of the three mononitrotoluenes. The MNT wastewater thus treated as an aqueous phase still had a residue content of dinitrocresols of 8 mg/l.

EXAMPLE 4

Nitration of Toluene to Dinitrotoluene with Addition of Dinitrocresol-Containing Toluene A 0.5 l four-neck flask with stirrer, reflux condenser, dropping funnel and thermometer was initially charged with a mixture of 65 g of toluene with 99.8% purity and 4 g of dinitrocresol-containing toluene (organic phase from example 1), approx. 120 mg of dinitrocresols having been present in the toluene. 167 g of a nitrating acid consisting of 53% by mass of 96% sulfuric acid, 40% by mass of 98% nitric acid and 7% by mass of water were slowly added dropwise with cooling without the temperature in the reaction mixture exceeding 45° C. Once the metered addition had ended, the mixture was stirred at 35° C. for a further 1 hour. After the phase separation at room temperature, the resulting mononitrotoluene was transferred as an organic phase to a 0.5 l four-neck flask with stirrer, reflux condenser, dropping funnel and thermometer, and 125 g of a nitrating acid consisting of 71% by mass of 96% sulfuric acid and 29% by mass of 98% nitric acid were slowly dropwise with cooling without the temperature in the reaction mixture exceeding 60° C. Once the metered addition had ended, the mixture was stirred at 60° C. for a further 1 hour. After the phase separation at 60° C., the resulting dinitrotoluene was washed as an organic phase twice by intensive stirring with 100 ml of distilled water and subsequent phase separation at 60° C. To remove the dinitrocresols, the washed dinitrotoluene was stirred intensively at 60° C. with 100 ml of a 5% sodium carbonate solution for 15 minutes. After the phase separation at 60° C., a dinitrocresol content of 582 mg/l was determined in the sodium carbonate solution (aqueous phase).

EXAMPLE 5

COMPARATIVE EXAMPLE

Nitration of Toluene to Dinitrotoluene without Addition of Dinitrocresol-Containing Toluene The procedure was as in example 4 except that, instead of the mixture of 65 g of toluene with 99.8% purity and 4 g of dinitrocresol-containing toluene, the feedstock used was now 69 g of toluene with 99.8% purity. After the phase separation at 60° C., a dinitrocresol content of 572 mg/l was determined in the sodium carbonate solution (aqueous phase).

The comparative example shows that the use of dinitrocresol-containing toluene in example 4 does not give rise to any significant increase of the dinitrocresols in the dinitrotoluene.

What is claimed is:

1. A process for preparing dinitrotoluene by nitration of toluene, which comprises providing a feedstock of nitrocresol-containing extracts obtained by removing nitrocresols from an alkaline wastewater of mononitrotoluene preparation, which comprises adding one or more acids to the alkaline wastewater of mononitrotoluene preparation to obtain a pH of at most 3 and treating the nitrocresols with an extractant then utilizing the extracted nitrocresols as a feed-stock in the preparation of dinitrotoluene.

2. The process according to claim 1, wherein the one or more acids have a $pK_a$ value of at most 2.

3. The process according to claim 1, wherein the one or more acids are mineral acids.

4. The process according to claim 1, wherein the nitrocresols are extracted with toluene, o-, m-, p-nitrotoluene or mixtures thereof.

5. The process according to claim 1, wherein the volume ratio of the wastewater to be extracted to the extractant is from 1:1 to 50:1.

6. The process according to claim 1, wherein the nitrocresol-containing extracts are added as a substream to the process stage of mononitration of toluene.

7. The process according to claim 1, wherein the nitrocresol-containing extracts are added as a substream to the process stage of dinitration.

8. The process according to claim 1, wherein the amount of nitrocresols added by the addition of the extracts is between 0.01 and 1% by weight based on the amount of dinitrotoluene obtained.

9. The process according to claim 2, wherein the acids are mineral acids.

10. The process according to claim 4, wherein the volume ratio of the wastewater to be extracted to the extractant is from 1:1 to 50:1.

11. The process according to claim 2, wherein the nitrocresol-containing extracts are added as a substream to the process stage of dinitration.

12. The process according to claim 2, wherein the acids are selected from nitric acid, sulfuric acid or a mixture thereof.

13. The process according to claim 1, wherein adding the one or more acids includes obtaining a pH of at most 2.

14. The process according to claim 5, wherein the volume ratio is from 2:1 to 10:1.

15. The process according to claim 6, wherein the extractant is toluene.

16. The process according to claim 7, wherein the extractant is 0-, m-, p-nitrotoluene.

17. A process for preparing dinitrotoluene by nitration of toluene according to claim 1,
   wherein nitrotoluene is used as an extractant; and
   adding the feedstock to the dinitrotoluene process such that the amount of nitrocresols added by the addition of the extracts is between 0.01 and 1% by weight based on the amount of dinitrotoluene obtained.

18. The process according to claim 17, wherein the volume ratio of the wastewater to the dinitrotoluene extractant is from 2:1 to 10:1.

* * * * *